US010016555B2

(12) United States Patent
Finch et al.

(10) Patent No.: US 10,016,555 B2
(45) Date of Patent: Jul. 10, 2018

(54) DIALYSIS BLOODLINE SET AND METHOD OF USE

(71) Applicant: Oxyless Limited, London (GB)

(72) Inventors: Steven Caffall Finch, London (GB); Franz Ferdinand Becker, Rodgau (DE)

(73) Assignee: OXYLESS LIMITED, London (GB)

( * ) Notice: Subject to any disclaimer, the term of this patent is extended or adjusted under 35 U.S.C. 154(b) by 47 days.

(21) Appl. No.: 15/143,980

(22) Filed: May 2, 2016

(65) Prior Publication Data

US 2016/0317731 A1 Nov. 3, 2016

(30) Foreign Application Priority Data

May 1, 2015 (GB) .................................. 1507540.1

(51) Int. Cl.
| *A61M 1/36* | (2006.01) |
| *A61M 1/16* | (2006.01) |
| *A61M 1/26* | (2006.01) |

(52) U.S. Cl.
CPC ........ *A61M 1/3643* (2013.01); *A61M 1/1621* (2014.02); *A61M 1/267* (2014.02); *A61M 1/365* (2014.02); *A61M 1/3627* (2013.01); *A61M 1/3639* (2013.01); *A61M 1/3644* (2014.02); *A61M 1/3646* (2014.02); *A61M 1/3649* (2014.02); *A61M 2205/3331* (2013.01)

(58) Field of Classification Search
CPC .. A61M 1/1621; A61M 1/267; A61M 1/3627; A61M 1/3639; A61M 1/3643; A61M 1/3644; A61M 1/3646; A61M 1/3649; A61M 1/365; A61M 2205/3331
See application file for complete search history.

(56) References Cited

U.S. PATENT DOCUMENTS

| 5,948,251 A | * | 9/1999 | Brugger ................ A61M 1/168 210/175 |
| 8,142,384 B2 | | 3/2012 | Becker |
| 2009/0036816 A1 | | 2/2009 | Becker |
| 2009/0071911 A1 | | 3/2009 | Folden |

FOREIGN PATENT DOCUMENTS

| EP | 2 883 558 | 6/2015 |
| GB | 1 527 380 | 10/1978 |
| WO | WO 03/055543 | 7/2003 |
| WO | WO 2013/138233 | 9/2013 |

OTHER PUBLICATIONS

Search Report dated Oct. 22, 2015 out of Great Britain priority Application No. I507540.1 (5 pages).

* cited by examiner

*Primary Examiner* — John Kim
(74) *Attorney, Agent, or Firm* — Brinks Gilson & Lione; John C. Freeman

(57) ABSTRACT

A dialysis bloodline set includes an arterial chamber with upper, lower and central portions, in which the maximum section area of the upper and central portions is less than that of the lower portion. The venous chamber may be completely filled with blood in use. The reduced volume of air within the bloodline provides, ceteris paribus, more rapid sensing of fault conditions during dialysis, while the smaller upper portion of the arterial chamber provides a useful medication point and makes manufacture easier.

7 Claims, 4 Drawing Sheets

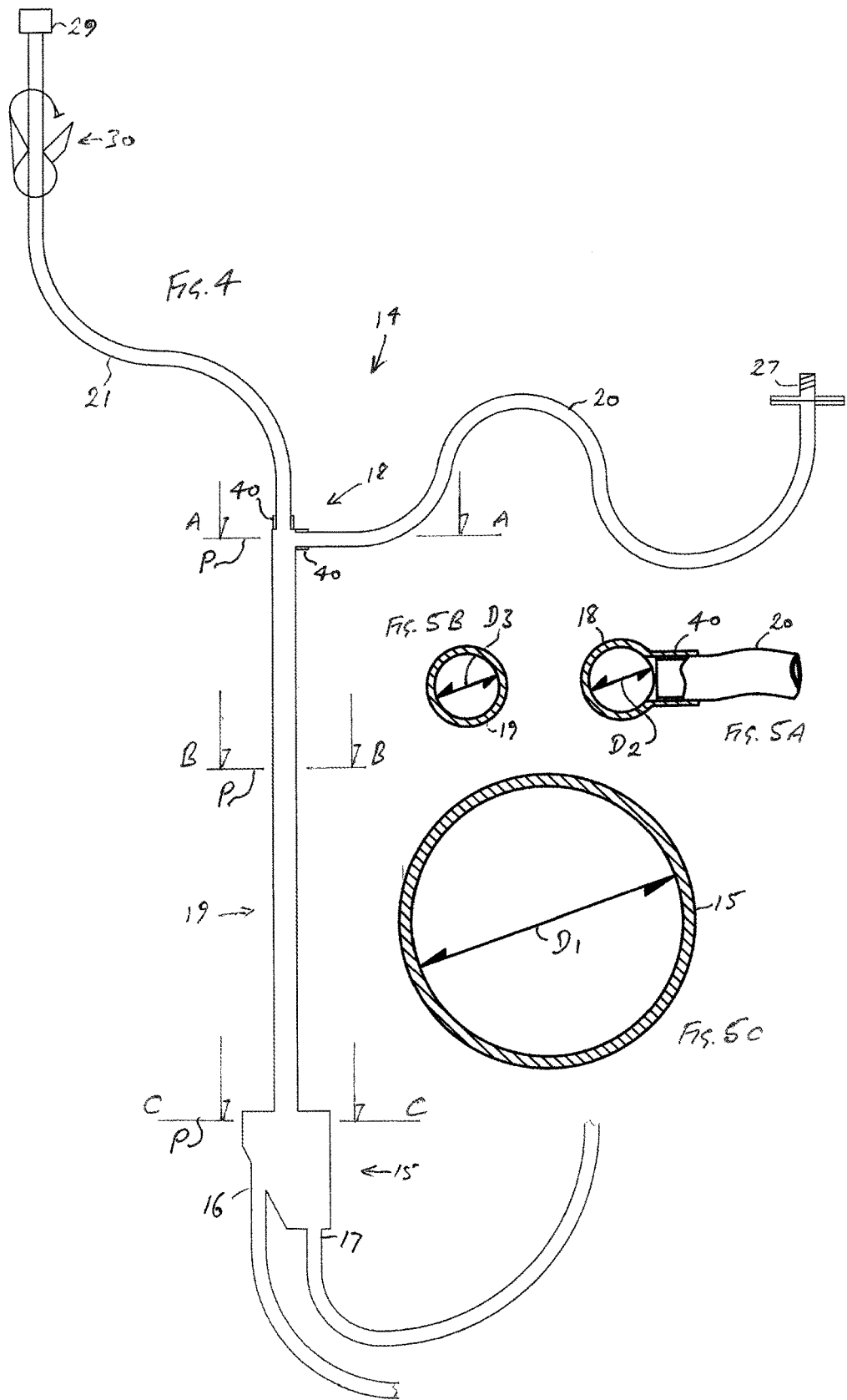

DIALYSIS BLOODLINE SET AND METHOD OF USE

This application claims priority to Great Britain Patent Application No. 1507540.1 filed on May 1, 2015, the entire contents of which is incorporated herein by reference.

BACKGROUND

This invention relates to bloodline sets for conveying a patient's blood to and from a dialyzer.

SUMMARY

In this specification, the term "dialysis" is taken to include hemodialysis, hemofiltration and hemodiafiltration, and the term "dialyzer" is construed mutatis mutandis to include a hemofilter.

The dialysis procedure requires three principal components: a dialyzer, a bloodline set (hereinafter referred to simply as a bloodline) comprising one or more tubing assemblies and associated components for connecting the dialyzer to the patient, and a dialysis machine for controlling the flow of blood and (in hemodialysis and hemodiafiltration) also the dialysate through the bloodline and the dialyzer.

A dialyzer comprises a semi-permeable membrane which separates blood from a dialysate or, in the case of hemofiltration, a filtrate compartment. Typically the membrane comprises a bundle of straws, each straw defining a lumen through which the blood flows. The dialyzer may be discarded after a single use or cleaned and re-used multiple times for the same patient.

Typically the bloodline is the simplest and least expensive part of the apparatus and is discarded after a single use.

The effectiveness of the dialysis procedure depends importantly on the transmembrane pressure (the difference in pressure between the blood on one side of the membrane and the dialysate or filtrate compartment on the other), which in turn is influenced by the flow resistance in the blood side of the circuit, which in turn varies with the flow rate of the blood responsive to the speed of rotation of the pump of the dialysis machine which urges the blood through the bloodline and the dialyzer and back to the patient.

Dialysis is a time consuming procedure and so it is desirable to maximize the flow rate of the blood through the dialyzer so that the patient receives the maximum possible benefit from each dialysis session. To achieve this, the dialysis machine is typically arranged to monitor and maintain at an optimal setting the transmembrane pressure and the speed of the pump, responsive to the inputs from a number of fluid pressure sensors which are fluidly connected to the blood flow through the bloodline via air filled tubes.

During dialysis, the flow resistance in the dialysis bloodline can change rapidly due to a number of causes including for example the presence of blood clots or other debris, variations in the rotational speed of the pump, displacement of the needles which connect the bloodline to the patient, and accidental misconfiguration or malfunction of the bloodline and other components of the dialysis procedure. In order to avoid discomfort or harm to the patient and damage to the dialyzer it is important that the dialysis machine should react quickly to such transient conditions, for example, by stopping or changing the speed of the pump.

The bloodline incorporates an arterial chamber and a venous chamber arranged respectively before and after the dialyzer in the direction of flow. In use, the blood flows through a lower portion of the arterial chamber so that a blood/air interface is formed in a central portion of the chamber above the lower portion. Contact with air at this interface activates the clotting cascade and so causes damage to the red blood cells. U.S. Pat. No. 8,142,384 teaches a bloodline in which the internal section area of the central portion of the arterial chamber is reduced to $\frac{1}{7}$ of that of the lower portion, whereby blood/air contact is substantially reduced so that less damage occurs to the red blood cells and the requirement for EPO, heparin and other drugs is concomitantly reduced.

It is also known from U.S. Pat. No. 8,142,384 that the venous chamber may be completely filled with blood, although in clinical practice it is normal for the upper part of the venous chamber to be filled with air. The blood drips through the air pocket so that any air bubbles entrained in the blood flow returning from the dialyzer are retained in the venous chamber.

The general object of the present invention is to provide a dialysis bloodline in which contact with air giving rise to damage to red blood cells is reduced and fault conditions giving rise to pressure fluctuations during dialysis can be rapidly detected.

Accordingly the invention provides a bloodline set and a method as defined in the claims.

BRIEF DESCRIPTION OF THE DRAWINGS

Further more specific objectives, features and advantages will be evident from the illustrative embodiments of the invention which will now be described, purely by way of example and without limitation to the scope of the claims, and with reference to the accompanying drawings, in which:

FIG. 4 shows the arterial chamber of the novel bloodline; and

FIGS. 5A, 5B and 5C are sections, each in a horizontal plane P, respectively, at lines A-A, B-B and C-C of FIG. 4.

Figure 1:
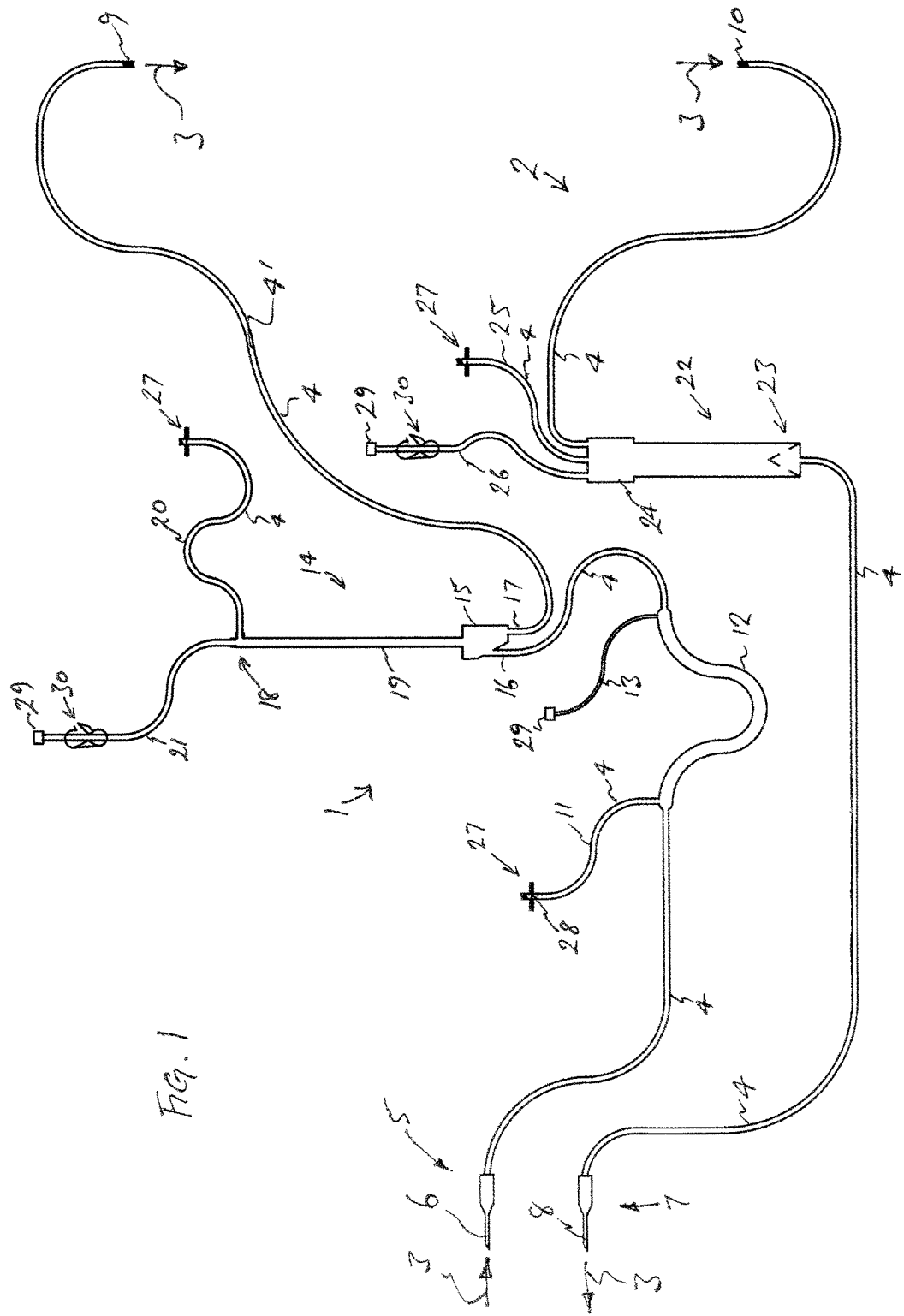
FIG. 1 shows a bloodline in accordance with a first embodiment of the invention.

Reference numerals appearing in more than one of the figures indicate the same or corresponding features in each of them.

DETAILED DESCRIPTION

Referring to FIG. 1, a bloodline comprises first and second sterile tubing assemblies 1, 2 made from flexible plastics material as known in the art and defining a flow path 3 through a bore 4' of the tubing 4 and other components of the bloodline for conveying blood to and from a patient via a dialyzer. The first tubing assembly 1 includes a patient inflow end 5 having a needle 6 which is inserted into a suitable access point (e.g. an arteriovenous fistula or catheter) to receive a flow of blood from the patient 100. The second tubing assembly 2 similarly has a patient outflow end 7 having a needle 8 for returning the flow of blood to the patient. In the illustrated example the inflow and outflow ends are separate but they could be combined into a single assembly as known in the art.

The first tubing assembly terminates in a dialyzer inlet connection 9 for connection to the inlet of a dialyzer, and the second tubing assembly terminates similarly in a dialyzer outlet connection 10 for connection to the outlet of the dialyzer. A plurality of auxiliary lines comprising pressure sensing lines, pressure balancing or vent lines, and injection lines are also fluidly connected to the flow path 3 at various points along the bloodline. Many of these auxiliary lines are adapted for more than one function, for example, to vent air from the bloodline and to provide an injection port through which drugs can be injected into the blood flow, as known in the art.

Between the inflow end 5 and the dialyzer inlet connection 9, the first tubing assembly includes a first pressure sensing line 11, an enlarged bore elastomeric silicone tubing section 12 to fit the peristaltic pump of the dialysis machine, a heparin injection line 13, and an arterial chamber 14.

Figure 3:
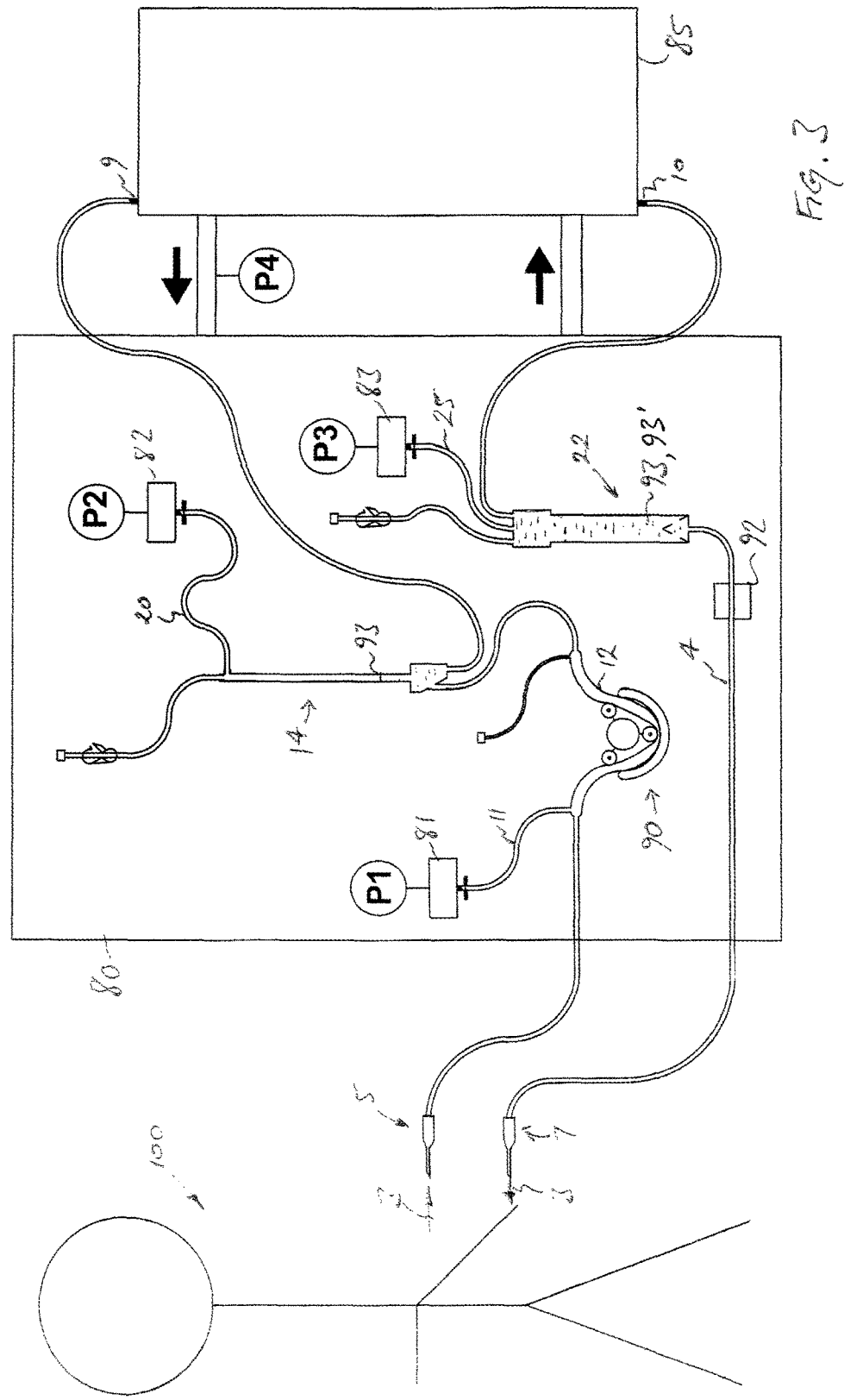
FIG. 3 shows the novel bloodline in use on the dialysis machine.

In the use position as shown in FIG. 3, the arterial chamber 14 comprises a lower portion 15, an upper portion 18, and a central portion 19 forming a vertical riser tube which is arranged between the lower portion and the upper portion. The lower portion includes an arterial chamber inflow connection 16 and an arterial chamber outflow connection 17 so that in use the flow path extends through the lower portion between the inflow and outflow connections and the blood circulates within the lower portion between them.

At least one of the auxiliary lines, and preferably two or more auxiliary lines are fluidly connected to the flow path 3, each via a respective auxiliary line connector extending outwardly from the upper portion of the arterial chamber. In the example shown, the upper portion 18 is arranged to form a manifold at the upper end of the riser tube, with two outwardly extending auxiliary line connectors 40. Two auxiliary lines comprising a second pressure sensing line 20 and an injection or pressure balancing line 21, also referred to as a vent line, are connected to the auxiliary line connectors which extend outwardly from the upper manifold portion 18.

Between the dialyzer outlet connection 10 and the patient outflow end 7 the second tubing assembly includes a venous chamber 22, which may have a filter at its lower outlet end 23 as shown. The upper inlet end 24 comprises a manifold to which are connected a third pressure sensing line 25 and an injection line 26.

Each of the pressure sensing lines terminates at a connector 27 with a gas permeable membrane 28 arranged to prevent the flow of blood but to transmit pressure via the column of air trapped in the tubing 4 of the pressure sensing line through the membrane to a pressure sensor of the dialysis machine. Each of the injection lines terminates at a removable cap 29 so that it can be used to introduce medication or other fluid into the blood during dialysis, or in the case of the injection line 21, to control the flow of air to and from the arterial chamber so as to regulate the level of blood in the riser tube. Depending on the type of dialysis machine, this function may also be performed automatically via the pressure sensing line 20.

Elastic plastics clips 30 are also provided on various ones of the lines, each clip being moveable between a locked position and an open position. In the locked position the clip compresses the tubing 4 so that the bore 4' is closed to prevent flow past that point. In the open position the bore 4' is unobstructed.

The bloodline need not include all the illustrated components, but will typically include other components in addition to those illustrated. For example, a bag for collecting saline solution may be releasably connected to the patient outflow end 7, with the tubing at that end being closeable by another clip 30 so that after priming the bloodline with a priming solution, typically a saline solution, and then displacing the saline solution as blood flows from the patient towards the patient outflow end 7, the patient outflow end can be sealed with the clip 30 before disconnecting the bag of used saline solution, and then re-connected to the patient before releasing the clip to allow blood to circulate through the dialyzer and back to the patient. Other conventional features will be familiar to those skilled in the art and are not described here in detail.

Figure 2:
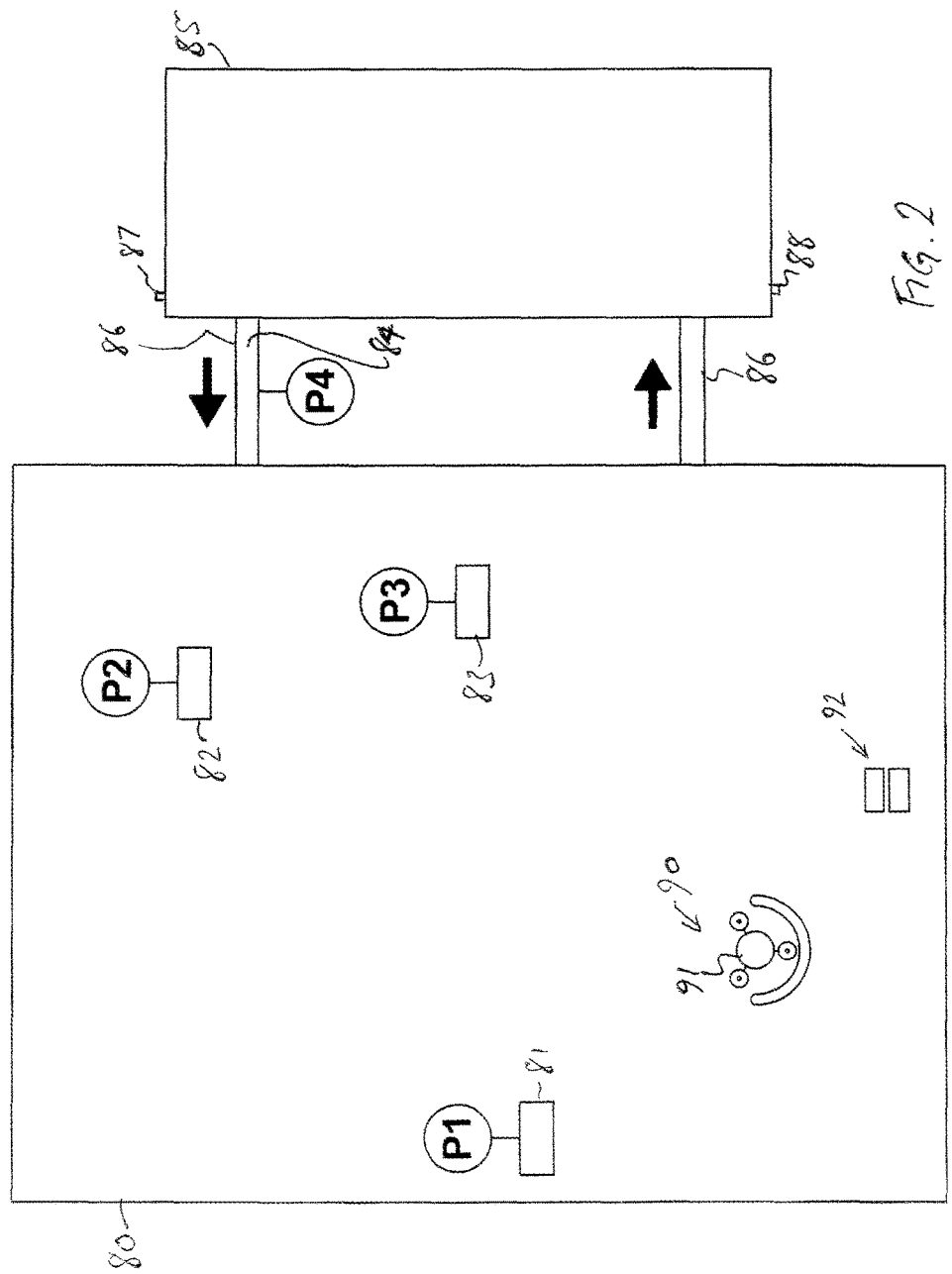
FIG. 2 shows a dialysis machine.

Referring to FIG. 2, the example dialysis machine 80 includes three pressure sensors having respective pressure sensing ports 81, 82, 83 for connection to the three connectors of the bloodline pressure sensing lines 11, 20, and 25 respectively. The fluid connection between each pressure sensing line and its point of connection with the blood flowing through the tubing 4 allows the dialysis machine to sense the fluid pressure P1, P2, P3 at each of those points. A peristaltic pump assembly 90 driven by a motor 91 is arranged to receive the tubing section 12 of the bloodline, and a bubble sensor 92 is arranged to receive the tubing 4 at the outlet end 23 of the venous chamber so as to sense any air entrained in the blood flow at that point.

The dialysis machine is connected via dialysate flow paths 86 to a dialyzer 85 through which it pumps the dialysate 84 in the direction indicated by the arrows. A fourth internal pressure sensor detects the fluid pressure P4 of the dialysate 84 in the dialyzer 85 or (where the dialyzer is a hemofilter) the pressure within the filtrate chamber. The dialyzer also has inlet 87 and outlet 88 connections for the bloodline.

Referring to FIG. 3, the bloodline is connected to the dialysis machine and to the dialyzer with the patient inflow and outflow ends connected to a suitable access point on the patient so that blood 93 can circulate from the patient via the dialyzer inlet and outlet connections 9, 10 which are connected to the inlet and outlet of the dialyzer so that the flow path 3 passes through the dialyzer and back to the patient. The connectors 27 of the pressure sensing lines are connected to the respective pressure sensing ports of the dialysis machine which controls the motor 91 of the pump.

Referring also to FIG. 4 and FIGS. 5A-5C, each portion of the arterial chamber has a maximum internal section area defined in a horizontal plane P in the use position. Both the upper portion 18 and the central portion 19 have maximum internal section areas less than that of the lower portion 15. In the example shown, the upper and central portions and the largest, upper part of the lower portion 15 are generally cylindrical and so their maximum internal diameters D1, D2, D3 respectively define their maximum internal section areas. The lower part of the lower portion 15 comprises an inclined base wall which encourages the desired circulatory flow path within the lower chamber as known in the art. In other embodiments the portions may have other tubular shapes, and their section area may also vary along the length axis of the arterial chamber.

Preferably both the upper portion and the central portion have maximum internal section areas not more than 50%, more preferably not more than 25%, most preferably not more than 15% of that of the lower portion.

In use, the bloodline may be primed, e.g. with saline solution, and the vent line 21 (or, where available, air pressure via sensing line 20) is used to regulate the level of the saline solution and subsequently the blood within the arterial chamber so that the lower portion 15 is filled with saline solution and subsequently with blood, while the blood/air contact interface is located in use part way up the riser tube defined by the central portion 19, as shown in FIG. 3. The upper portion 18 and the portion of the riser tube 19 above the contact interface are filled with air. The reduced section area of the central portion 19 minimizes the area of the blood/air contact interface to reduce oxidation of the blood during dialysis.

Advantageously, the upper portion 18 may have a maximum internal section area not greater than that of the central portion 19. The reduced section area of the upper portion 18 compared with that of the lower portion 15 reduces the volume of air within the bloodline in use. This in turn means that any fault condition resulting in a change in pressure will cause more rapid pressure fluctuation at the pressure sensors upstream of the dialyzer, including where provided the pressure sensor to which the pressure sensing line 20 is connected, than would be the case with a prior art arrangement in which the upper portion of the arterial chamber is typically of the same section area as the lower portion. The novel bloodline thus results in a faster response from the dialysis machine if a fault develops during a dialysis session.

A further advantage of the reduced section area of the upper portion is observed where (rarely) a medication is introduced into the injection line 21 via port 29. In the event that the medication is of relatively small volume, prior art arterial chambers may retain a significant proportion of that volume as a film on the internal surface of the air-filled upper portion. By reducing the section area of the upper portion, the arterial chamber can be used as a more reliable entry point for small volume medications.

Although it is entirely conventional for an arterial chamber to have an upper portion of the same diameter as the lower portion, the Applicant has found that in normal modern clinical practice it is unnecessarily voluminous and, contrary to established convention, may advantageously be reduced in size.

The volume of the remaining air filled portions of the bloodline may be generally similar to that found in prior art bloodlines, except for the venous chamber which advantageously may be substantially completely filled with blood 93 during dialysis as shown in FIG. 3. This removes the blood/air interface conventionally present in the venous chamber and so further reduces oxidation of the blood, and further enhances the response time of the dialysis machine by reducing the compressible volume of air downstream of the dialyzer which otherwise delays the triggering of the pressure sensor via pressure sensing port 83 to which the venous chamber sensing line 25 is connected.

When preparing the dialysis machine and dialyzer for dialysis, the novel bloodline is connected to the dialysis machine and to the dialyzer before filling the flow path 3 with a priming solution 93'. At this time the venous chamber is substantially completely filled with the priming solution 93' as also shown in FIG. 3, conveniently by venting air from the vent line 26 as the priming solution flows through the bloodline. The bloodline is then connected to the patient and the venous chamber is substantially completely filled with blood as the blood flows through the bloodline and displaces the priming solution.

The arterial chamber of the novel bloodline may be manufactured from readily available tube connections, wherein the upper portion may comprise for example a T connector, which simplifies manufacture compared with the prior art chamber.

Although in the illustrated embodiment the tubing section 12 which in use is acted upon by the pump assembly is arranged upstream of the arterial chamber 14, it will be understood that in alternative embodiments the tubing section 12 could be arranged instead elsewhere in the bloodline set, such as downstream of the arterial chamber 14 between the arterial chamber 14 and the dialyzer 85, in which case the action of the pump may be sensed as a negative rather than positive pressure.

In summary, a dialysis bloodline set includes an arterial chamber with upper, lower and central portions, in which the maximum section area of the upper and central portions is less than that of the lower portion. The venous chamber may be completely filled with blood in use. The reduced volume of air within the bloodline provides, ceteris paribus, more rapid sensing of fault conditions during dialysis, while the smaller upper portion of the arterial chamber provides a useful medication point and makes manufacture easier.

The novel bloodline is preferably disposable, but could be re-usable after cleaning and disinfection. The bloodline could include a single tubing assembly or more than two tubing assemblies. Those skilled in the art will appreciate that many other adaptations are possible within the scope of the claims.

The invention claimed is:

1. A bloodline set for conveying blood to and from a patient via a dialyzer, the bloodline set being in a use condition and comprising:

at least one assembly of tubing defining a flow path for the blood;

a patient inflow end for receiving a flow of blood from the patient;

a patient outflow end for returning the flow of blood to the patient;

dialyzer inlet and outlet connections for connecting the tubing respectively to an inlet and an outlet of a dialyzer so that the flow path passes through the dialyzer;

an arterial chamber arranged between the patient inflow end and the dialyzer inlet connection;

a venous chamber arranged between the dialyzer outlet connection and the patient outflow end; and a plurality of auxiliary lines fluidly connected to the flow path;

the arterial chamber comprising in a use position a lower portion, an upper portion, and a central portion arranged between the lower portion and the upper portion;

the lower portion including an arterial chamber inflow connection and an arterial chamber outflow connection so that the flow path extends through the lower portion between the inflow and outflow connections;

at least one said auxiliary line being fluidly connected to the flow path via a respective auxiliary line connector extending outwardly from the upper portion of the arterial chamber;

each portion of the arterial chamber having a maximum internal section area defined in a horizontal plane in the use position;

wherein both the upper portion and the central portion have maximum internal section areas less than that of the lower portion and the bloodline set is connected in its use condition to a patient so that the flow path including at least the lower portion of the arterial chamber is filled with blood from the patient to define a gas/liquid interface located between an upper part of the central portion and a lower part of the central portion, the upper portion and the upper part of the central portion being filled with air above the gas/liquid interface.

2. A bloodline set according to claim 1, wherein both the upper portion and the central portion have maximum internal section areas not more than 50% of that of the lower portion.

3. A bloodline set according to claim 1, wherein both the upper portion and the central portion have maximum internal section areas not more than 25% of that of the lower portion.

4. A bloodline set according to claim 1, wherein both the upper portion and the central portion have maximum internal section areas not more than 15% of that of the lower portion.

5. A bloodline set according to claim 1, wherein the upper portion has a maximum internal section area not greater than that of the central portion.

6. A bloodline set according to claim 1, wherein the venous chamber is substantially completely filled with blood.

7. A method of dialysis, including:
providing a bloodline set according to claim 1;
connecting the bloodline set to the dialyzer;
connecting the bloodline set at the patient inflow and outflow ends to the patient and filling the flow path including the lower portion of the arterial chamber with blood from the patient; and
regulating a level of the blood within the arterial chamber to define a gas/liquid interface between the upper part of the central portion and the lower part of the central portion, wherein the upper portion and the upper part of the central portion are filled with air above the gas/liquid interface.

* * * * *